United States Patent [19]
Doms et al.

[11] Patent Number: 5,648,833
[45] Date of Patent: Jul. 15, 1997

[54] MOTORIZED INSTRUMENT FOR THE EXAMINATION OF HUMAN EYES

[75] Inventors: Manfred Doms; Ulrich Fischer, both of Saalfeld, Germany

[73] Assignee: Block Medizintechnik GmbH, Saalfeld, Germany

[21] Appl. No.: 502,223

[22] Filed: Jul. 13, 1995

[30] Foreign Application Priority Data

Jul. 19, 1994 [DE] Germany .................. 44 25 443.1

[51] Int. Cl.⁶ ................................................. A61B 3/02
[52] U.S. Cl. ........................... 351/235; 351/233; 351/234
[58] Field of Search ................................. 351/234, 235, 351/229, 228, 246, 222

[56] References Cited

U.S. PATENT DOCUMENTS 4,496,225  1/1985  Augusto ...................... 351/234
4,798,457  1/1989  Morohashi et al. ........... 351/235

FOREIGN PATENT DOCUMENTS 3331799  3/1984  Germany.
3833342  4/1990  Germany.
4127163  2/1993  Germany.

OTHER PUBLICATIONS

New Type of Piezoelectric Ultrasonic Motor by Fleischer et al –IEEE Transactions on Ultrasonics, Ferroelectrics, and Frequency Control, vol. 36, No. 6 Nov. 1989.

Primary Examiner—Hung X. Dang
Attorney, Agent, or Firm—Jordan and Hamburg

[57] ABSTRACT

A phoropter comprises two observation channels, in each of said observation channels a plurality of disk-shaped mounts, rotatably seated about at least one axis, for mounting optically effective members and drive means for rotating said mounts. The drive means are piezoelectric motors, each of which is, on the one hand, connected to a base and, on the other hand, provided with a driving end portion, preferably a driven member which executes a rotating motion. The driven member is, compared to the piezoelectric motor, of small design.

14 Claims, 2 Drawing Sheets

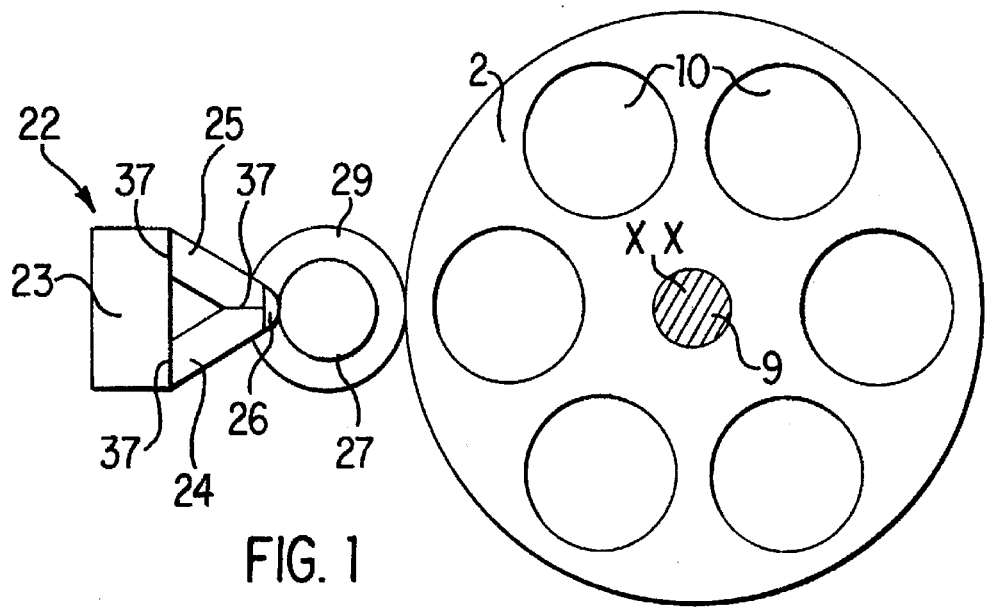
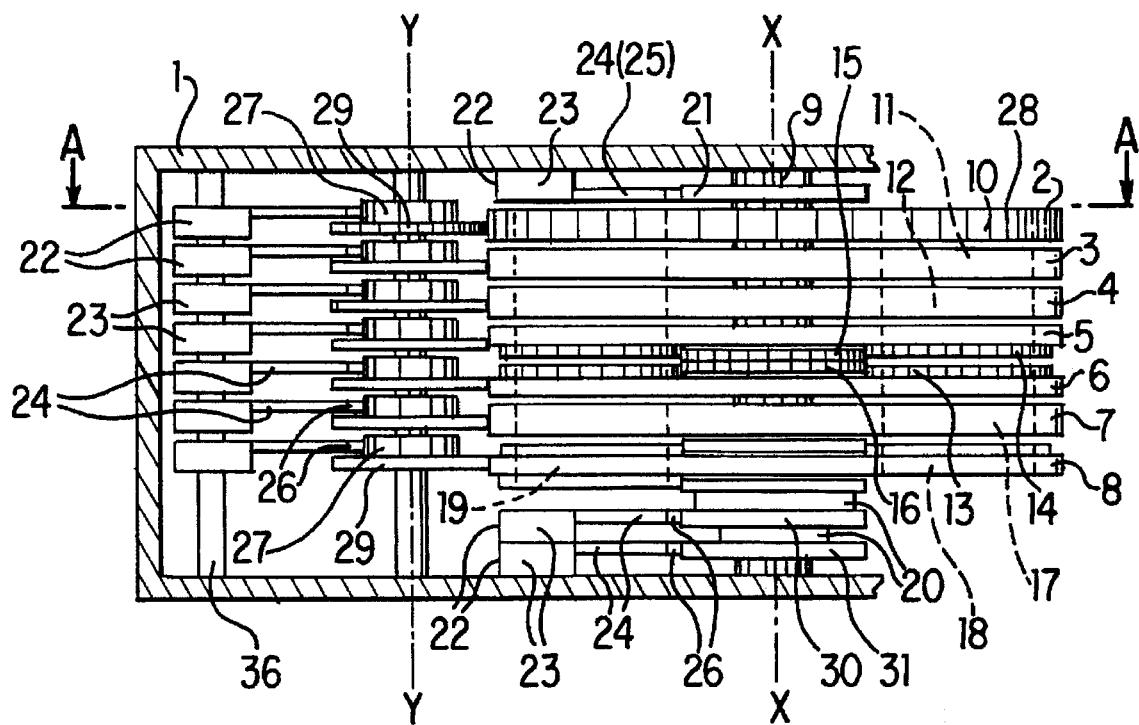

MOTORIZED INSTRUMENT FOR THE EXAMINATION OF HUMAN EYES

BACKGROUND OF THE INVENTION

The invention relates to a phoropter for determining deficiency of sight of the human eye and the prescription of vision aids, respectively. In known devices for examination of the human eyes spherical lens mounts and frame elements for cylindrical lenses are rotated by means of electrical rotation means, refer to DE 33 31 799 A1, for example, to render them operative in a required combination in a vision window. Typically, synchronous motors or stepper motors are employed as electrical rotation means to operate the mounts and the frames, respectively, via belt-driven guide rollers or gear wheels. The known rotation devices are material and space-consuming and, hence, are responsible for covering a large part of a patient's face by the phoropter used in the course of an examination.

A further known piezoelectric motor (DE 38 33 342 A1) comprises a drive member and a driven member friction coupled to the former; the drive member excites two orthogonal components of motion in the range of the friction contact, one of the components effects the proper drive and the other one the contact. The drive member includes two exciting systems which are electrically and magnetically operated, respectively, and are separated from one another resulting in an unduly large space-consuming mass.

In a further known piezoelectric motor at least two piezoelectric crystal yokes are arranged in a rotatably seated drive drum secured to a frame which yokes abut against the interior face of the drum (DE 41 27 163 A1). These arrangements are very expensive and not applicable for phoropters.

SUMMARY OF THE INVENTION

It is an object of the present invention to provide a compact phoropter by virtue of a new drive adapted to the special conditions in which the drive permits a bi-directional rotation of the mounting disks relative to the axes of rotation at a moderate speed.

It is feasible to attach a preferably bulged friction range to the drive end portion of the piezoelectric motor via which the drive means acts upon the disk-shaped mount. It is, however, also feasible to adhere a driven member having a respectively shaped surface to the drive end portion of the piezoelectric motor. In this event the driven member is small compared to the piezoelectric motor, that is, its mass is insignificant relative to the piezoelectric motor mass and, hence, does not damp the inherent frequency of the piezoelectric motor. When, for example, it is difficult to work the drive end portion owing to the material used or when a connection means is required, then it is advantageous to provide a driven member on the drive end portion of the piezoelectric motor. During a rotation cycle, each drive is intermittently frictionally connected via its drive end portion with the mount to be driven. It is advantageous when each electrostrictional and magnetostrictional, respectively, piezoelectric motor includes two respective operative members supplied with a phase-shifted a.c. voltage, preferably shifted by $\pi/2$. The resulting substantially circular motion of the drive end portion is employed to transmit, via its portion in opposition to the disk-shaped mount, a forward motion and, via its portion averted from the disk-shaped mount, a reverse motion. To simplify assembly it is advantageous to mount the piezoelectric motors, via their bases partially or entirely on a common support arranged in analogy to the disk mount array. It is feasible to arrange the two piezoelectric members in parallel to one another. However, an advantageous embodiment is obtained when each piezoelectric member is secured via an equally positioned end portion to a base and both piezoelectric elements which are connected to the same base are inclined towards each other via their other end portion and are connected to one another via the driven member. The operation of the piezoelectric motor is rendered stable and safe by flexibly mounting the drive member or, at least, by a flexible embodiment of the junction between the electrostrictive members with one another and with their base.

It is feasible to directly transfer the drive operation from the electrostrictive and the magnetostrictive, respectively, piezoelectric motors upon the mounting disks. This requires, however, that the seating of the mounting disks as well as their rigidity are axially and radially stable enough. The mounting disks have to be seated with a low friction, preferably by means of ball bearings and, hence, would have a width which renders the mounting disk housing of the phoropter bulky at the dioptric observation passage. This disadvantageous effect is aggravated when the ball-bearing race at least partially projects axially from out of the mounting disk planes and when the electrostrictive drives are arranged between the mounting disks. Therefore it is more favourable to insert respective motion transfer means between the piezoelectric motors and the mounting disks and the drive wheels, respectively, for the axles and shafts. The motion transfer means preferably are ball-seated small gear wheels, the ball-bearings of which axially project from out of the plane of the small gear wheels. The ball-bearing outer races are rigid enough to resist deformations resulting from impacts caused by piezoelectric motions. The small gear wheels mesh with the gear rims of the mounting disks and the drive wheels on the common axle of the mounting disks, respectively, and the hollow shafts, respectively, enclosing the axle. When the piezoelectric motors do not ensure a time-proportional consistency of the drive paths, it is advantageous to provide marks on the disk-shaped mounts cooperating with a detecting means which is adapted to determine the motion steps of the optically effective members and of the initial position. Thus, it is feasible to adjust the zero-position, the dioptric observation passage which is free from optical members and, starting from this position, to set precisely any desired optical member into the observation channel by rotating the disk mounts and the drive wheels, respectively. In an advantageous embodiment each disk shaped mount is provided with magnets equally spaced along its periphery, and with a further magnet inserted between two adjacent magnets, the further magnet being unequally spaced from the two adjacent magnets. A magneto-resistant resistor is provided as a detector in the vicinity of the periphery of the corresponding disk-shaped mount. When a magnet passes the midposition the magneto-resistant resistor delivers a high steepness of slope pulse which indicates the exact alignment of the centre of the optically effective member with the optical axis of the observation channel.

BRIEF DESCRIPTION OF THE DRAWINGS

The invention is explained in more detail by virtue of the accompanying schematical drawings which show in FIG. 1 a top view of an arrangement of mounting disks and of the corresponding drive means along a line A—A in FIG. 2, FIG. 2 a sideview of mounting disks with drive means, and FIG. 3 a mounting disk with marks.

DETAILED DESCRIPTION OF THE INVENTION

Figure 3:
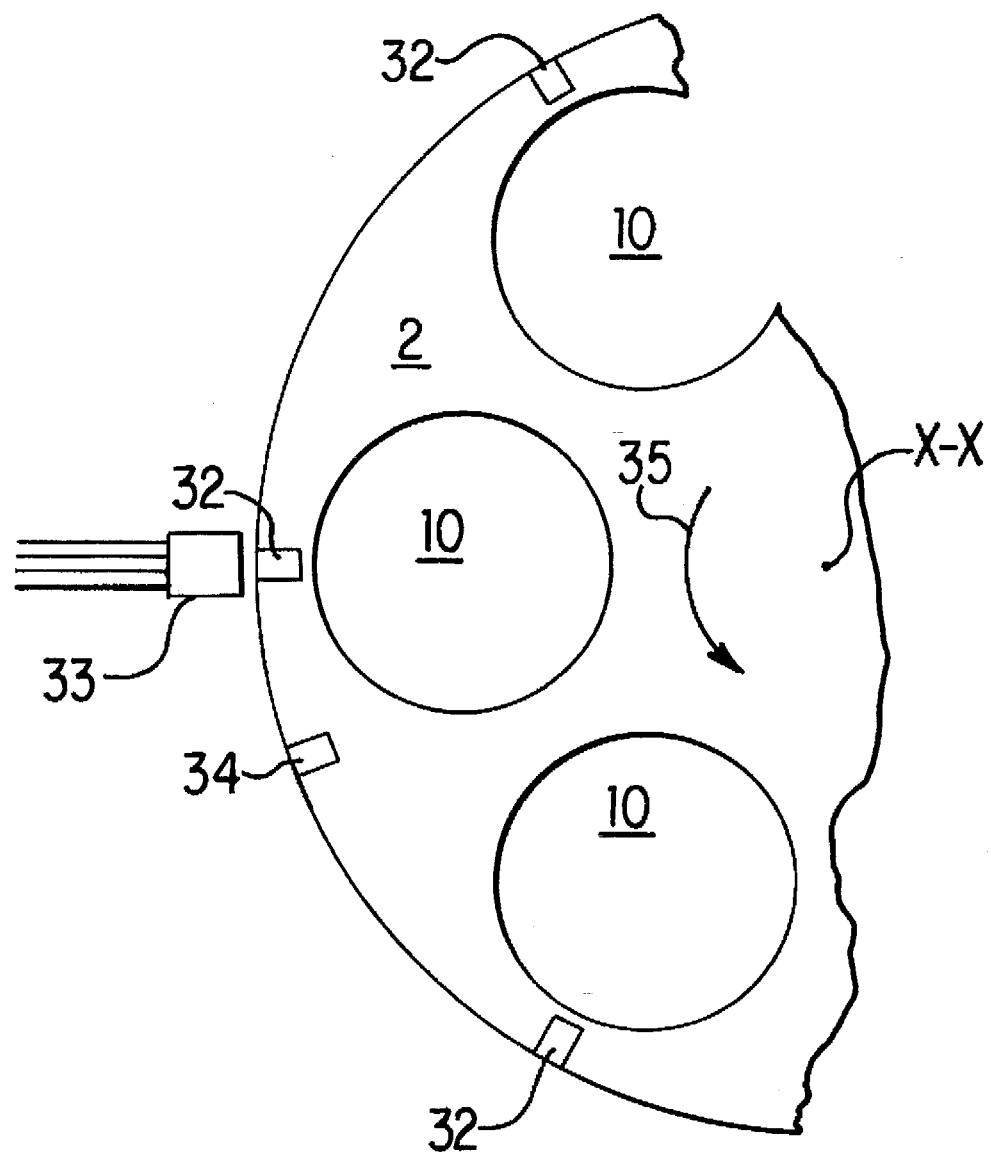

In FIGS. 1 and 2 light-transmissive disk-shaped mounts 2 to 8 of equal diameters are arranged coaxially to and seated for rotation about an axis X—X in a partially shown phoropter housing 1. The diameter of the mounting disks 2 to 8 is 75 mm. The mounting disks 2, 3, 4 are rotationally seated on a shaft 9 and are provided with openings 10, 11, 12 for supporting spherical lenses of various diopter values which can be combined with one another between +23.25 D and −30.5 D in 0.25 D steps. Each of the mounting disks 5, 6 supports four cylindrical lenses seated in gear rims 13, 14, said cylinder lenses can be combined with one another and are adapted to set 0 to −6 D in 0.25 D steps. The gear rims 13, 14 are engaged with the gear wheels 15, 16 which are secured to the shaft 9 and which have substantially the same diameter as the gear dins 13, 14. The mounting disk 7 is seated for rotation about the shaft 9 and is provided with additional optical members (filter, Maddox cylinder, apertures, occluders, centering means) arranged in respective openings 17. Finally, the mounting disk 8 exhibits, in addition to a free dioptric passage 18 which also comes true for the other mounting disks 2 to 7, two openings 19 for supporting two cross cylinders and two rotary prisms (not shown in detail). By operation of hollow shafts 20 the cross cylinders and the rotary prisms are driven. Electrostrictive drive means are employed to drive the shaft 9, the gear rims 13, 14, and the hollow shafts 20. A wheel 21 is press fitted to the shaft 9 and is operatively connected to an elctrostrictive piezoelectric motor 22 which, in turn, is permanently connected to a housing. The piezoelectric motor 22 is comprised of a base 23 and, pivotally attached thereto, are two mutually inclined electrostrictive rods 24, 25 which are connected to one another by a driven member 26 acting upon the wheel 21. A phase-shifted a.c. voltage is applied across the two electrostrictive rods 24, 25 produces a circular and longitudinal motion which the driven member 26 transmits via its face to the wheel 21, thus effecting the rotation of wheel 21 and, consequently, of the shaft 9. The phase-shift of the a.c. voltage is optionally $\pi/2$. The rotation figure of the driven member is a circle; it can also be an ellipse tangently directed to the wheel 21. The electrostrictive piezoelectric motors 22 comprised of the base 23, the rods 24, 25 and the driven member 26 are the same for the mounting disks 2 to 8 as well as for the cross cylinders and rotary prisms in the openings 19. The mounting disks 2 to 8, provided with gear rims 28 on their peripheries, are driven by their piezoelectric motors 22 via the ball bearing 27 seated gear wheels 29, thus moving the desired optical members into the observation channel. The ball bearing 27 and the gear wheel 29 are seated coaxially to mid for rotation about an axis Y—Y. It is obvious that the outer race of the respective ball bearing 27 is best suited, when dimensioned respectively, to consistently transmit the driving forces to the respective mounting disk. When rotating the mounting disks 5, 6 by operation of the respective piezoelectric motors 22 the gear rims 13, 14 mesh the gear wheels 15, 16 substantially at a 1:1 transmission ratio. All piezoelectric motors 22 are rigidly and superjacently mounted in a block-system 36 in the housing 1.

The block-system 36 is oriented substantially in parallel to the shaft 9. The widths of the piezoelectric motors 22 are advantageously equal to the width of the mounting disks 2 to 8. Hence, the piezoelectric motors 22 are arranged in a common plane with the respective mounting disk 2 to 8 driven by the former. The axial extension of the block-system 36 equals the shaft extension 9. Such an arrangement substantially contributes to minimize the phoropter housing 1 size.

Flexible junctions 37 are provided between the base 23 and the electrostrictive members 24, 25 and, further, between the two electrostrictive members 24 and 25. To drive the hollow shafts 20 magnetostrictive piezoelectric motors 22 secured to the housing 1 are employed to actuate wheels 30, 31, mounted on the hollow shafts 20, and thus rotate the cross cylinders and the rotary prisms, respectively, provided in the openings 19 (only one visible). In this manner a fine adjustment of astigmatism and a determination of the amount of strabismus is obtained.

The material for the mounting disks 2 to 8 can be light transmissive or opaque. It is advantageous when the material for the mounting disks is light transmissive, however, non-transparent for simulating the vision habits in the course of an eye examination with a phoropter. The gear rims 28 at the periphery can be made of a different material than that of the mounting disks. The ball-bearing outer races 27 have a width of 1 mm so that they are not deformed by impact motions of the piezoelectric motor 22. The gear wheels 29 are made of metal, preferably aluminum. Unlike the arrangement in FIG. 2 it is feasible to arrange the piezoelectric motors laterally displaced relative to the disks 2 to 8 and to one another. In an alternative embodiment of the invention the intermediate wheels 29 can be omitted and the piezoelectric motors 22 actuate the wheels 21, 30, 31 via intermediate gear wheels. The material of the members 24, 25 can be selected from crystals or from layers of electrostrictive ceramics or any other suitable material to the outer layers of which electrodes are attached for example by bonding, for applying a voltage. Typically, two members 24, 25 have to be provided to permit the feeding of a reversible phase delayed voltage, thus stimulating a rotary motion of the driven member 26 and of the respective face. The reversibility of two phase delayed voltages applied effects a drive reversal. Finally, the piezoelectric motors comprised a block-system can be resiliently mounted in as a whole assembly.

In FIG. 3, a mounting disk, exemplified by the mounting disk 2, is sectionally shown and is provided with, for example, magnetic marks which are distributed in equal angular spaces on the mounting disk 2. Each mark 32 designates an opening 10. The marks 32 cooperate with a detector, for example, a magneto-resistive member 33, which is nondisplaceably attached to the device, and which, when the mounting disk 2 is rotated parallel to the drawing plane and in the direction indicated by an arrow 35, delivers pulses to a control center (not shown). Furthermore, an additional mark 34 is provided beween two adjacent marks 32 for detecting an initial position of rotation of the mounting disk 2. The arrangement operation is as follows: at a deviation of the pulse sequence from the pattern of the pulse sequence produced by the marks 32 a subsequent pulse will be produced by the "zero" mark, provided that the space is larger then half the space between two adjacent marks 32. When the space is smaller than half the distance between adjacent marks 32 then the preceding mark 32 is "zero". This is relevant for rotations of the mounting disk 2 in opposition direction to that indicated by the arrow 35. Thus, any possible errors of function of the piezoelectric motor 2 are eliminated. What was said with respect to the rotation of the mounting disk 22 is also pertinent to the mounting disks 3 to 8.

Alternatively, instead of deriving the zero marks (free dioptric passage) on the mounting disks 2 to 8 direction dependent it is also feasible that after starting operation of the phoropter the mounting disks at first or generally rotate in a definite direction to detect the zero position before the measurements start.

It is also feasible to replace the magnetic marks in FIG. 3 by optical or mechanical marks cooperating with respective detectors or feelers.

We claim:

1. A motorized instrument for the examination of human eyes, comprising:

an instrument body having two apertures defining two observation channels;

a plurality of disk-shaped mounts for supporting optical members alignable with said two observation members, said disk-shaped mounts being rotatably supported on said instrument body about at least one axis;

piezoelectric motors, each of said piezoelectric motors being arranged adjacent to a respective disk-shaped mount of said disk-shaped mounts and coupled to rotate said respective disk-shaped mount in the plane of said respective disk-shaped mount;

each of said piezoelectric motors having a base secured to said instrument body and a circulating driven face; and said driven face being coupled to said respective disk-shaped mount and being arranged on a driven member small compared to said piezoelectric motor.

2. The motorized instrument as claimed in claim 1, wherein each of said piezoelectric motors is provided with two electrostrictive members across which a phase-shifted a.c. voltage is applied.

3. The motorized instrument as claimed in claim 2, wherein the a.c. voltage is phase-shifted by $\pi/2$.

4. The motorized instrument claimed in claim 1, wherein the piezoelectric motors are arranged in a block-system and oriented in parallel to planes of the disk-shaped mounts.

5. The motorized instrument as claimed in claim 4, wherein each electrostrictive member is secured via a first end portion thereof to said base at spaced apart positions and said electrostrictive members are mutually inclined to have second end portions thereof connected to one another via the driven member.

6. The motorized instrument as claimed in claim 5, wherein the piezoelectric motors are elastically seated.

7. The motorized instrument as claimed in claim 6, wherein elastic junction are provided between the base, the elctrostrictive members, and the driven member.

8. The motorized instrument as claimed in claim 1, wherein a motion transmitter couples each driven face and the respectively coordinated disk-shaped mounts.

9. The motorized instrument as claimed in claim 1, wherein the disk-shaped mounts are made of light transmissive material.

10. A motorized instrument for the examination of human eyes, comprising:

an instrument body having two apertures defining two observation channels;

a plurality of disk-shaped mounts for supporting optical members alignable with said two observation members, said disk-shaped mounts being rotatably supported on said instrument body about at least one axis;

piezoelectric motors, each of said piezoelectric motors being arranged adjacent to a respective disk-shaped mount of said disk-shaped mounts and coupled to rotate said respective disk-shaped mount in the plane of said respective disk-shaped mount:

each of said piezoelectric motors having a base secured to said instrument body and a circulating driven face;

each of said driven faces being coupled to said respective disk-shaped mount and being arranged on a driven member small compared to said piezoelectric motor;

motion transmitters coupling each of said driven faces with said respective disk-shaped mounts; and each of the motion transmitters being a gear wheel meshing with a gear rim provided on a periphery of the disk-shaped mounts, the gear wheel being non-rotationally connected to an outer race of a ball bearing, and an outer surface of said outer race being driven by an actuating face of the driven face.

11. The motorized instrument as claimed in claim 10, wherein the disk-shaped mounts are provided with marks cooperating with a detector for sensing motion steps indicative of movement of said optical members as well as of the initial positions of said optical members.

12. The motorized instrument as claimed in claim 10, wherein each disk-shaped mount is provided along its periphery at equal spaces with magnets, a further magnet is inserted between two of said equally spaced magnets and is unequally spaced relative to the two equally spaced magnets, and further comprising a magnetoresistive resistor disposed proximate the periphery of said respective disk-shaped mount for sensing movement and position of said disk-shaped mounts.

13. A motorized instrument for the examination of human eyes, comprising:

an instrument body having two apertures defining two observation channels;

a plurality of disk-shaped mounts for supporting optical members alignable with said two observation members, said disk-shaped mounts being rotatably supported on said instrument body about at least one axis;

piezoelectric motors having a thickness in the axial direction of said disk-shaped mounts substantially equal to or less than a thickness of said disk-shaped mounts, each of said piezoelectric motors being disposed adjacent to and within a common plane of a respective disk-shaped mount of said disk-shaped mounts and coupled to rotate said respective disk-shaped mount in the plane of said respective disk-shaped mount;

each of said piezoelectric motors having a base secured to said instrument body and a circulating driven face; and said driven face being coupled to said respective disk-shaped mount and being arranged on a driven member small compared to said piezoelectric motor.

14. The motorized instrument according to claim 13, wherein said piezoelectric motors are disposed in-line with each other in said axial direction of said disk-shaped mounts.

* * * * *